United States Patent [19]

Yamamoto et al.

[11] Patent Number: 5,470,732
[45] Date of Patent: Nov. 28, 1995

[54] RESTRICTION ENZYME FROM BREVIBACTERIUM LINENS

[75] Inventors: Katsuhiko Yamamoto; Hiroaki Sagawa, both of Otsu; Hirokazu Kotani, Muko; Nobutsugu Hiraoka, Matsudo; Teruya Nakamura, Kusatsu, all of Japan

[73] Assignee: Takara Shuzo Co., Ltd., Japan

[21] Appl. No.: 688,426

[22] Filed: Apr. 22, 1991

[30] Foreign Application Priority Data

Apr. 20, 1990 [JP] Japan .................................. 2-106231

[51] Int. Cl.⁶ .............................. C12P 19/34; C12N 9/22; C12N 1/00
[52] U.S. Cl. ...................... 435/196; 435/71.1; 435/71.2; 435/840; 435/843
[58] Field of Search ................................ 435/71.1, 71.2, 435/196, 840, 843

[56] References Cited

FOREIGN PATENT DOCUMENTS 45093   5/1988   Hungary .

58-107172   6/1983   Japan .

*Primary Examiner*—Marian C. Knode
*Assistant Examiner*—Jon P. Weber
*Attorney, Agent, or Firm*—Wenderoth, Lind & Ponack

[57] ABSTRACT

A restriction enzyme is obtained by cultivating a strain of *Brevibacterium linens* and recovering the restriction enzyme. The restriction enzyme, which has the same specificity as AvrII, cleaves the following nucleotide sequence specifically at the arrow-marked sites:

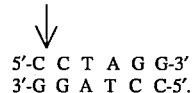

1 Claim, No Drawings

RESTRICTION ENZYME FROM *BREVIBACTERIUM LINENS*

This invention relates to a restriction enzyme. More particularly, it relates to a process for producing a restriction enzyme by the cultivation of a microorganism belonging to the genus Brevibacterium.

Restriction enzymes are endonucleases that are capable of recognizing a specific nucleotide sequence of in a deoxyribonucleic acid (DNA) molecule and cleaving the double-stranded DNA at specific sites. As a result of the stranded DNA at specific sites. As a result of the progress in the molecular genetics, biochemistry and related sciences, DNA proved to hold the key to the hereditary constitution of living bodies, and since then restriction enzymes have been extensively used as useful enzymes for various purposes, such as clarification of genetic diseases and mass-production of useful substances by genetic manipulation. Restriction enzymes have been isolated from a variety of microorganisms, and about 150 kinds are known at present, each being identified by the specific nucleotide sequence it recognizes and by the cleavage pattern it exhibits. As a restriction enzyme capable of recognizing the following nucleotide sequence and cleaving it at the arrow-marked sites:

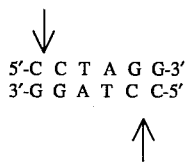

```
5'-C T A G G-3'
3'-G G A T C C-5'
```

(wherein C, T, A and G represent cytidine, thymidine, adenosine and guanosine, respectively), is known Avr produced by Anabaena variabilis UW [Gene, Vol. 7, p. 217–270 (1979)].

This $A_{vr}$ II-producing microorganism is an alga, which is difficult to cultivate and produces $A_{vr}$ II in a very low yield; hence, the use of this microorganism is not amenable to industrial production.

The object of this invention is to provide a method of producing a restriction enzyme capable of recognizing and cleaving the same base sequence as $A_{vr}$ II, which is amenable to industrial production.

Briefly, this invention relates to a process for producing a restriction enzyme, which comprises growing a microorganism belonging to the genus Brevibacterium and capable of producing a restriction enzyme that specifically cleaves the following nucleotide sequence at the arrow-markted sites, and recovering said restriction enzyme from the culture broth:

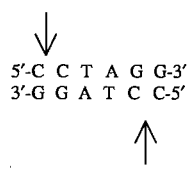

```
5'-C T A G G-3'
3'-G G A T C C-5'
``` wherein C, T, A and G represent cytidine, thymidine, adenosine and guanosine, respectively.

The present inventors found that a restriction enzyme capable of recognizing and cleaving the same specific nucleotide sequence as $A_{vr}$ II can be produced in a large amount by the cultivation of a microorganism belonging to the genus Brevibacterium, and that said microorganism does not produce any restriction enzyme other than $A_{vr}$ II and hence the enzyme formed can be easily purified. This invention was accomplished on the basis of these findings.

This invention will be described below in more detail.

Any microorganism belonging to the genus Brevibacterium and capable of producing said restriction enzyme may be used in the process of this invention. As an example, may be mentioned *Brevibacterium linens* IAM1902 stored at the Applied Microorganism Laboratory in Tokyo University and deposited at the Fermentation Research Institute, Agency of Industrial Science and Technology, under FERM BP-2870.

The culture medium used in the process of this invention contains a proper combination of carbon resources, nitrogen resources, inorganic salts and other nutrients which the microorganism used will assimilate to produce the restriction enzyme. Its pH should preferably be in the range from 5.0 to 9.0. Any of shake culture, agitation culture and aeration culture may be adopted, but cultivation with aeration and agitation is preferred for mass-production. The culture temperature may be in the temperature range that ensures production of the restriction enzyme, but a range from 20° to 33° C. is the most preferred. The optimal cultivation time Varies depending on the culture conditions adopted, and cultivation should be continued until the yield of the restriction enzyme reaches its maximum.

The restriction enzyme produced by the process of this invention is chiefly accumulated inside the microbial cells, and the grown cells can be isolated from the culture broth, for example, by centrifugation.

The enzyme formed can be isolated and purified by using known techniques commonly employed for restriction enzymes. The collected microbial cells are dispersed in a buffer solution, the cell walls were broken down by ultrasonic treatment, and the accumulated enzyme is extracted. After removal of the residue by ultracentrifugation, the extract is treated with 1% streptomycin to remove nucleic acids, and ammonium sulfate is then added for salting out. The precipitate which separates out is collected and dissolved in a Tris-HCl buffer solution (pH 7.5), and the solution is dialyzed against the same buffer solution. The dialyzate is then purified by ion-exchange chromatography using phosphocellulose and hydroxyapatite, or by affinity chromatography using heparine-Sepharose, thus giving the restriction enzyme of this invention.

The activity of this enzyme was determined according to the method described below. A substrate solution of the composition shown in Table 1 below was prepared.

TABLE 1

| | |
|---|---|
| 10 mM | Tris-HCl, pH 7.5 |
| 7 mM | $MgCl_2$ |
| 7 mM | 2-Mercaptoethanol |
| 100 mM | NaCl |
| 1.0 μg | λ-DNA (product of Takara Shuzo Co. Ltd.) |

This solution (50 μl) was preheated to 37° C., a sample of the enzyme of this invention to be tested was then added to allow the enzymatic reaction to proceed at that temperature, and the reaction was stopped 60 minutes later by adding 5 μl of a terminator solution (containing 1% SDS, 50% glycerol, and 0.02% Bromophenol Blue). The reaction mixture was applied to a 1% agarose slab gel, and electrophoresis was conducted at a constant voltage of 10 V/cm for about one to two hours. The buffer solution used for electrophoresis was 90 mM Tris-borate buffer containing 2.5 mM EDTA (pH 8.3). DNA bands can be detected by UV irradiation if 0.5 μg/ml ethidium bromide is previously added to the gel. Electrophoresis was regarded as complete when the number and intensity of the bands for DNA fragments no longer changed.

The enzyme activity which ensures complete digestion of 1 μg λ-DNA after one hour's reaction at 37° C. was defined as one unit.

The restriction enzyme obtained by the process of this invention has the physicochemical properties as described below.

(1) Action and substrate specificity

This enzyme is capable of recognizing the nucleotide sequence in a double-stranded DNA molecule as shown below and cleaving it at the arrow-marked sites, and is therefore an isoschizomer of the known restriction enzyme $A_{vr}$ II.

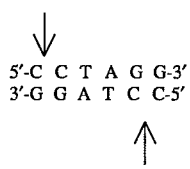

The base sequence recognized by the restriction enzyme of this invention was determined by using, as substrate, λ-DNA, pBR322 DNA and φX 174RFI DNA (products of Takara Shuzo Co., Ltd.) as well as adenovirus-2 DNA (product of Bethesda Research Laboratories). The result was that the restriction enzyme of this invention cleaved λ-DNA at two sites and adenovirus-2 DNA at two sites, but failed to cleave pBR322 DNA and φX 174RFI DNA. In addition, the known restriction enzyme, $A_{vr}$ II, was allowed to act upon these substrates, and the cleavage patterns thus obtained were compared with those of the restriction enzyme of this invention, demonstrating the same patterns between the two types of enzymes. These data led to the conclusion that the nucleotide sequence in DNA molecules which the restriction enzyme of this invention recognizes is 5'-CCTAGG-3'.

The sites of cleavage by the restriction enzyme of this invention was determined by recovering a single-stranded DNA from a vector prepared by introducing 5'-GC-CTAGGC-3' (a nucleotide sequence including 5'-CCTAGG-3' which is the sequence recognized by the restriction enzyme of this invention) to M13 mp 18 RFI DNA (product of Takara Shuzo Co., Ltd.), annealing it with a primer of 5'-GTTTTCCCAGTCACGAC-3' (SEQUENCE ID NO: 1) labelled with $^{32}$p at 5' end, synthesizing a double-stranded chain by the use of E. coli DNA polymerase I Klenow fragment, cleaving the double-stranded DNA thus obtained by the restriction enzyme of this invention, and measuring the chain length of fragments thus formed by electrophoresis on a modified polyacrylamide gel. The obtained product was detected as a spot formed by cleavage at the arrow-marked site of

leading to the conclusion that the enzyme of this invention recognizes the following nucleotide sequence and to cleave it at the arrow-marked sites.

(2) Optimal conditions for enzymatic activity a) Optimal temperature

The optimal temperature was approximately 37° C.

b) Optimal pH

The optimal pH was in the range from 7.0 to 8.5.

c) Salt concentration

The optimal salt concentration was in the range from 50 to 150 mM in the case of NaCl.

d) MgCl$_2$ concentration

The enzymatic reaction of the restriction enzyme of this invention was activated at a MgCl$_2$ concentration in the range from 5 mM to 20 mM.

e) Molecular weight

The molecular weight of the restriction enzyme of this invention was 96000±4000 daltons when measured by the gel filtration method using Sephadex G-100, and was 42000±2000 daltons when measured by electrophoresis on SDS-polyacrylamide gel. This indicates that this enzyme is a dimeric enzyme composed of two subunits having a molecular weight of about 45000 daltons.

The following Example will further illustrate this invention but is not intended to limit its scope.

Example 1

Twenty liters of a culture medium having the composition shown in Table 2 below was put in a 30-liter jar fermenter and sterilized by the method commonly employed.

TABLE 2

| Glucose | 1 g |
| Yeast extract | 5 g |
| Polypeptone | 10 g |
| Sodium chloride | 5 g |
| Deionized water | 1 l |
| pH | 7.2 |

Inoculum (500 ml) of *Brevibacterium linens* IAM 1902, (FERM BP-2870) deposited on Apr. 16, 1990 at the Fermentation Research Institute, Agency of Industrial Science and Technology, 1-3, Higashi 1-chome, Tsukuba-shi, Ibaraki-ken 305, Japan, obtained by shake culture in a medium having the same composition as above at 30° C. for 24 hours, was placed in the above jar fermenter, and cultivation was conducted at 30° C. for 18 hours with aeration (1 vvm) and agitation (250 rpm). The grown cells were collected from the culture broth by using a refrigerated centrifuge (about 144 grams of grown cells on wet basis from 20 liters of the culture broth).

Seventy-two grams of the microbial cells obtained above were suspended in 360 ml of Suffer solution A (containing 20 mM Tris-HCl (pH 7.5), 10 mM 2-mercaptoethanol and 5% glycerol), the suspension was treated in a ultrasonic crusher to break down the cell walls, and the resulting mixture was centrifuged (100,000×g, one hour) to remove the residue.

To the extract thus obtained (400 ml), was added 4 g of streptomycin, and the mixture was allowed to stand at 4° C.

for one hour and centrifuged (10,000×g, 10 minutes). To the supernatant thus obtained, was added ammonium sulfate to 80% saturation, the precipitate which separated out was collected by centrifugation and dissolved in buffer solution A further containing 0.2M KCl, and the solution was dialyzed overnight against the same buffer solution as above.

The dialyzate was then adsorbed on 100 ml of phosphocellulose (product of Whatman Co.) packed in a column and previously equilibrated with buffer solution A containing 0.2M KCl. After washing with the same buffer as above, the adsorbed portion was eluted with buffer solutions A containing 0.2M to 1.0M KCl (linear concentration gradient technique). The active fractions thus obtained were mixed together, the combined solution was then adsorbed on 30 ml of hydroxyapatite (Bio-rad Laboratories Ltd.) packed in a column and previously equilibrated with 10 mM potassium phosphate buffer solution, and the adsorbed portion was eluted with 10 mM to 500 mM potassium phosphate buffer solutions (linear concentration gradient technique). The active fractions thus obtained were mixed together, the combined solution was dialyzed for four hours against buffer solution A, and the dialyzate was once more adsorbed on heparine-Sepharose (product of Pharmacia Fine Chemicals Inc.) previously equilibrated with buffer solution A. After thoroughly washing with the same buffer as above, the adsorbed portion was eluted with buffer solution A containing 0.8M KCl, affording the standard sample of the restriction enzyme of this invention.

This standard sample was free from any nonspecific DNase or phosphatase.

The purification method described above gave 800,000-unit activity from 72 g of wet microbial cells.

As is apparent from the foregoing, this invention provides an industrially advantageous process for producing a restriction enzyme capable of recognizing and cleaving the same base sequence as $A_{vr}$ II.

---

What we claim is:

1. A process for producing a restriction enzyme which comprises cultivating a strain of *Brevibacterium linens* having all the identifying characteristics of *Brevibacterium linens* IAM 1902 (FERM BP-2870) under conditions sufficient to produce said restriction enzyme, and recovering said restriction enzyme, wherein said restriction enzyme cleaves the following nucleotide sequence specifically at the arrow-marked sites:

$$\downarrow$$
5'--- C C T A G G ---3'
3'--- G G A T C C ---5'.
$$\uparrow$$

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:

( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:1:

GTTTTCCCAG TCACGAC 17